United States Patent [19]

Barnes et al.

[11] Patent Number: 4,688,935
[45] Date of Patent: Aug. 25, 1987

[54] PLASMA SPECTROSCOPIC ANALYSIS OF ORGANOMETALLIC COMPOUNDS

[75] Inventors: Ramon M. Barnes, Hadley, Mass.; Istvan Bertenyi, Budapest, Hungary

[73] Assignee: Morton Thiokol, Inc., Chicago, Ill.

[21] Appl. No.: 507,597

[22] Filed: Jun. 24, 1983

[51] Int. Cl.$^4$ .................... G01N 1/00; G01N 33/22
[52] U.S. Cl. ........................... 356/36; 356/316; 436/76; 436/179
[58] Field of Search .............. 436/72, 76, 166, 179; 356/316, 36; 250/287, 288, 282; 73/864.81, 1 R, 1 G; 422/83, 68

[56] References Cited

U.S. PATENT DOCUMENTS

| | | | |
|---|---|---|---|
| 3,824,016 | 7/1974 | Woodrief | 356/85 |
| 3,888,628 | 6/1975 | Graham | 436/132 |
| 3,911,723 | 10/1975 | Ritter | 73/1 R |
| 3,922,475 | 11/1975 | Manasevit | 156/613 X |
| 4,259,573 | 3/1981 | Prober et al. | 250/282 X |
| 4,300,393 | 11/1981 | Barnes et al. | 73/863.11 |
| 4,334,882 | 6/1982 | Edwards | 23/230 |
| 4,454,095 | 6/1984 | Holt | 422/83 X |

FOREIGN PATENT DOCUMENTS 0106443 6/1983 Japan ................................ 422/83

OTHER PUBLICATIONS

ICP-Atomic Emission Spectrometry as a Tool for Flexible Single-Element Analysis of Non-Routine Samples, Boumans et al., Fresenius Z. Anal. Chem. 291 10-19 (1978).
Plasma Emission Spectral Detection for High-Resolution Gas Chromatographic Study of Group IV Organometallic Compounds, Estes et al., J. Chromatography, 239 (1982) 181-189.
Direct Current Atmospheric Pressure Argon Plasma Emission Echelle Spectrometer as a Specific Metal Gas Chromatographic Detector, Barnes et al., Anal. Chem., vol. 50, No. 14 (1978) 2025.
Hanamura et al.; Speciation of Inorganic and Organometallic Compounds in Solid Biological Samples by Thermal Vaporization and Plasma Emission Spectroscopy, Anal. Chem. 1983 55(13), 2026-32 CA99:154664a.
Barnes; Recent Advances in Analytical Atomic Radiofrequency Emission Spectroscopy Phil. Trans. R. Soc. Lond. A 305, 499-508 (1982).
Ritter et al.; Exponential Dilution as a Calibration Technique: Anal. Chem., vol. 48, No. 3 3/76 612-9.
Inman et al.; Calibration Curve Preparation of Analytes in Liquid Solutions by Means of an Exponential Dilution Flask; Applied Spectroscopy, vol. 36, No. 2, 1982, 99-102.
Porterfield, *Concepts of Chemistry*, Norton & Co., Inc., New York, 1979, pp. 382-389.
Patents Abstracts of Japan, vol. 7, No. 212 (P-224) (1357) Daini Seikosha K.K. Sep. 1983 58-106443.
Analytical Chemistry, vol. 55, No. 4, Apr. 1983, pp. 802-805.
E. Kitazume: "Thermal Vaporization for One-Drop Sample Introduction into the Inductively Coupled Plasma".
Japanese Patent Abstract 57-26734 5/26/82.
Analytical Chemistry, vol. 55, No. 13, Nov. 1983, pp. 2026-2032.

*Primary Examiner*—Barry S. Richman
*Assistant Examiner*—Michael S. Gzybowski
*Attorney, Agent, or Firm*—George F. Wheeler; Gerald K. White

[57] ABSTRACT

A method of analyzing a volatile, air or moisture sensitive or pyrophoric, liquid, organometallic compound for an impurity comprising inserting a sample of the compound into an exponential dilution flask, allowing substantially the entire sample to vaporize, and analyzing the vapor by plasma spectroscopy; or decomposing the sample by dropwise addition into frozen aqueous acid, diluting the decomposed sample with water, and analyzing the diluted, decomposed sample by plasma spectroscopy.

9 Claims, 4 Drawing Figures

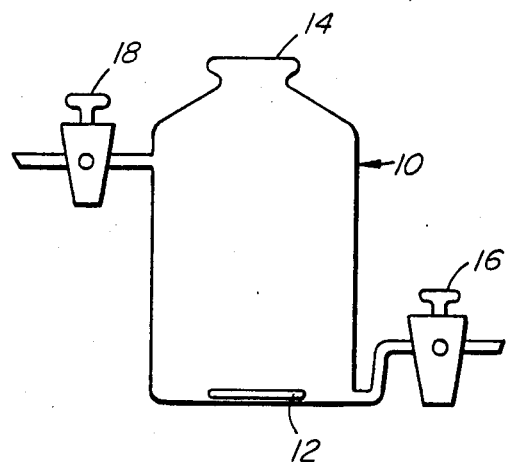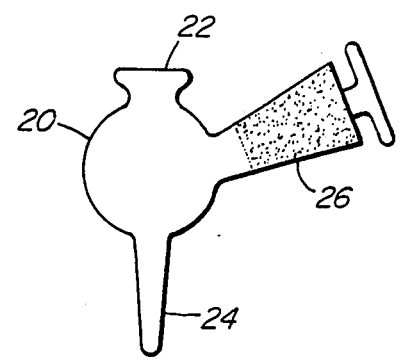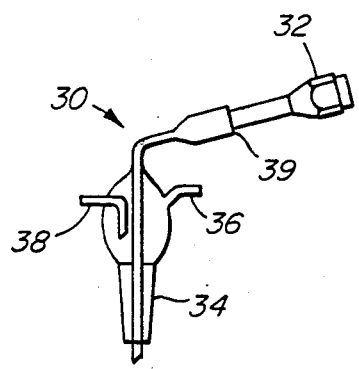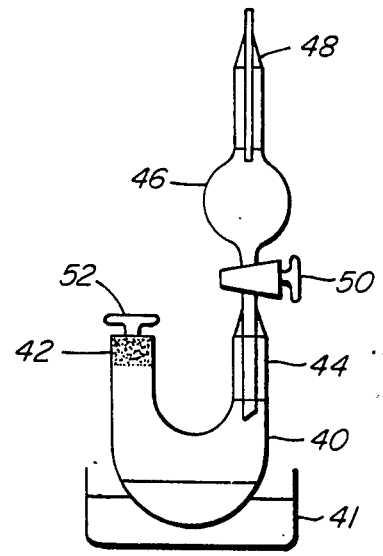
FIG. 1
FIG. 2
FIG. 3
FIG. 4

PLASMA SPECTROSCOPIC ANALYSIS OF ORGANOMETALLIC COMPOUNDS

BACKGROUND OF THE INVENTION

1. Field of the Invention

The present invention relates to analysis of organometallic compounds, and more particularly, analysis of organometallic compounds which are air or moisture sensitive, or pyrophoric.

2. Description of the Prior Art

Metal alkyls of Groups II, III and IV are used in combination with metal hydrides and alkyls of Groups V and VI for the formation of semiconductor materials and alloys by means of chemical vapor deposition. The purity levels of these highly reactive organometallic compounds is of primary importance, because contaminating elements in the $\mu g/g$ range may completely alter the properties of the semiconductor materials formed.

However, the extreme reactivity of these organometallic compounds makes analysis of trace impurities very difficult. For example, trimethylgallium is typical in that it is a liquid which reacts pyrophorically with air and moisture. Thus, analysis of such a compound must be performed under an inert atmosphere or the compound must be decomposed prior to analysis. Both of these methods have been used in the prior art with limited success.

Decomposition methods are typically directed to forming oxides of the compound and any impurities. One procedure for decomposing trimethylgallium (TMG) is to add a small volume of TMG to several times that volume of hexane, and then decompose the TMG behind a blast shield in a fume hood. Distilled deionized water is added dropwise until about twice as much water by volume has been added as the original volume of TMG. A heat gun is used to evaporate the hexane. When the hexane vapor is replaced by water vapor, the heat gun is replaced by a torch and the sample is heated at a temperature of about 300-400° C. until a free flowing oxide is generated. This oxide is then analyzed by various well known techniques, such as direct current arc emission spectroscopy.

An alternative decomposition procedure is to simply ignite a small aliquot of TMG behind a blast shield in a fume hood. After each aliquot has ceased burning, an additional aliquot is treated similarly until a sufficient sample of oxide is obtained for analysis.

Both of the above decomposition methods suffer from the limitation that the heat of oxide formation results in the loss of most of any volatile oxides which are generated, as well as the possibility that materials which oxidize slowly will be vaporized prior to conversion to oxide. These limitations are particularly problematical when it is considered that the more volatile impurities are more likely to be incorporated into the product during chemical vapor deposition.

An alternative method has attempted determination of impurities by direct analysis of the organometallic by dissolution in a suitable organic solvent (e.g., methyl isobutyl ketone, xylenes, methanol/ethanol, or toluene), followed by nebulization and analysis by inductively coupled plasma-atomic emission spectroscopy (ICP-AES).

A nebulizer is used to mix the sample to be analyzed with a suitable gas, e.g., argon. As the sample is ejected from the outlet of the nebulizer, discrete droplets are obtained which continue within the gas stream into the ICP unit. Only about 5–10% of the liquid which enters the nebulizer forms individual droplets of a size that they are carried into the ICP unit. It has been assumed that the remainder of the liquid simply falls out of the stream entering the ICP unit where it passes into a drain and is collected.

This latter method suffers from the disadvantage that it must be assumed that the droplets entering the ICP unit are representative of the sample being tested, and this is not the case, especially when organic solvents are being used for the analysis of TMG. It must also be assumed that none of the solvent or analyte vapors enter the ICP except as droplets.

Accordingly, a need existed for a method of analyzing air or moisture sensitive or pyrophoric organometallic compounds without the concomitant disadvantages of the prior art.

SUMMARY OF THE INVENTION

The present invention is a method of analyzing a volatile, air or moisture sensitive or pyrophoric, liquid, organometallic compound for impurities. In one embodiment, the present invention comprises inserting a sample of the compound into an exponential dilution flask, allowing substantially the entire sample to vaporize, and analyzing the vapor by plasma spectroscopy. This embodiment is particularly useful for determining volatile impurities In another embodiment, the sample of the organometallic compound is decomposed by dropwise addition into frozen aqueous acid, diluted with water, and then analyzed by plasma spectroscopy. This embodiment is especially useful for mesuring nonvolatile impurities.

BRIEF DESCRIPTION OF THE DRAWINGS

FIG. 1 is a side view of an exponential dilution flask for use in the method of the present invention FIG. 2 is a side view of a container for sampling an air-or moisture-sensitive or pyrophoric material in air.

FIG. 3 is a side view of an adapter for removing a samle of an air- or moisture-sensitive or pyrophoric matrial from a storage container.

FIG. 4 is a side view of an apparatus for decomposing a sample of an air- or moisture-sensitive or pyrophoric matrial according to another embodiment of the present invention.

DETAILED DESCRIPTION OF THE INVENTION

In one embodiment of the present invention, a sample of the organometallic compound to be analyzed is inserted into an exponential dilution flask where substantially it is allowed to vaprize completely before being analyzed by plasma spectroscopy.

As discussed above, in the prior art, a nebulizer was use to produce droplets for introduction of the sample into the ICP unit. That method is based upon the assumption that the small proportion of droplets which enter the ICP unit are representative of the liquid sample entering the nebulizer. It has now been discovered that that assumption is not true for at least certain impurities which are found in organometallic compounds.

In particular, certain organosilicon compounds of high volatility appear to be vaporized preferentially during nebulization. This vapor is then swept along with the droplets by the carier gas to produce an erroneously high silicon impurity reading in the resulting analysis. However, this problem has not been previously recognized.

The following comparative experiments illustrate the effect of volatility on the amount of impurity measured. In each case a standard solution of a silicon compound is prepared in xylene. Other suitable solvents include hexane, toluene, and methyl isobutyl ketone. Three compounds are chosen as follows:

Comparative Sample A: Tetravinylsilane (TVS) (liquid; f.w. 136; b.p. 130° C.)
Comparative Sample B: Tetramethylsilane (TMS) (liquid; f.w. 88; b.p. 23° C.)
Comprative Sample C: Diphenylsilanediol (DPS) (solid; f.w. 216; m.p. 130–150° C.)

Comprative Samples A–C are diluted in xylene to 0.5 p.p.m. (parts per million), 1.0 p.p.m. and 2.0 p.p.m. of silicon. Two replicates with Samples A and B and one replicate with Sample C are performed. Testing is performed on a commercially available ICP-AES unit (PlasmaTherm Generator, Model HFS-5000D; Minuteman Monochrometer, Model 310-SMP, 1200 l/mm grating) with the following signals being measured:

| Concentration in terms of Si | Measured Signal (n Amperes) | | | | |
|---|---|---|---|---|---|
| | TVS | | TMS | | |
| | 1 | 2 | 1 | 2 | DPS |
| 0.5 ppm | 0.14 | 0.14 | 4.7 | 4.5 | 0.032 |
| 1.0 ppm | 0.29 | 0.31 | 7.8 | 7.8 | 0.068 |
| 2.0 ppm | 0.58 | 0.63 | 16.6 | 16.5 | 0.14 |
| SLOPE (nA/ppm) | 0.29 | 0.32 | 8.1 | 8.1 | 0.073 |

The above is a standard method for obtaining a calibration curve. However, instead of obtaining a single curve of a given slope, each compound provides a different slope, and the most volatile compound (TMS) gives the highest slope, while the least, essentially nonvolatile, compound (DPS) gives the lowest slope. The slope is a direct measure of the determination sensitivity.

Further evidence for the effect of volatility on the measurement of impurities is seen by a comparison of the signal from nebulized original sample versus nebulized sample collected from the drain of the original sample which is then used as the pseudo-sample in a second test. The results are as follows:

| Solution | Silicon Signal (nAmp) | |
|---|---|---|
| | original sample | pseudo-sample |
| Xylene | 2.23 | 2.20 |
| 2 ppm Si (DPS) | 2.65 | 2.68 |
| 2 ppm Si (TVS) | 8.35 | 6.0 |
| 2 ppm Si (TMS) | 101 | 16.5 |

The signals from the original solution and the drain solution acting as a pseudo-sample are significantly different except for the diphenylsilanediol, again indicating that the concentration of silicon in the drain solution is lower than in the original solution and that the volatility of the silicon compound is affecting the original sample from the nebulizer.

To overcome this problem, the present invention employs an exponential dilution flask. Such flasks are known to those skilled in the art for purposes other than impurity determination in air- and moisture-sensitive and pyrophoric compounds, and any such flask can be used in practicing the method of the present invention. For example, a suitable flask is described in Inman et al, "Calibration Curve Preparation of Analytes in Liquid Soluion by Means of an Exponential Dilution Flask", *Applied Specroscopy*, Vol. 36, No. 2, pages 99–102 (1982), as a means of avoiing serial dilution for the preparation of standards. Anoter description of the design and use of exponential dilution flasks is Ritter et al, "Exponential Dilution as a Calibration Technique," *Analytical Chemistry*, Vol. 48, No. 3, pages 612–619 (1976).

However, due to the air and moisture sensitivity or pyrophoric nature of the compounds to be analyzed by the present method, it is preferred to use an exponential dilution flask such as that in FIG. 1. Exponential dilution flask 10 contains a magnetic stirring bar 12 for ensuring a homogeneous atmosphere inside flask 10 after a liquid sample has been injected by a syringe through septum 14. The carrier gas, which can be any inert gas but is preferably argon, enters through stopcock 16 and exits through stopcock 18 which is in the line leading to a plasma, such as an inductively coupled plasma. Stopcocks 16 and 18 are initially opened to purge flask 10, and then closed for addition of the sample through septum 14. A bypass (not shown) is arranged such that gas flows from stopcock 16 to stopcock 18, i.e. around flask 10, to provide a reference signal and to allow the sample in flask 10 to evaporate before sampling is performed. All of the materials coming into contact with the sample must be inert to the sample. Flask 10 is preferably made of glass and stopcocks 16 and 18 are preferably teflon. Flask 10 and the various other connections can also be made of teflon if desired.

By allowing the sample substantially to vaporize completely prior to plasma treatment, it is assured that the sample is more closely representative of the vapor being used during chemical vapor deposition. Even if a small amount of impurity does not vaporize in the dilution flask, it is unlikely to affect the production of materials by chemical vapor deposition since its low vapor pressure would also probably result in little vaporization during deposition. To ensure that as much of the sample vaporizes as possible, the magnetic stirrer (not shown) used to spin stirring bar 12 is equipped with a heater. In the case of trimethylgallium, the flask is typically heated to between about 40° and about 50° C. To provide a sample for analysis at an appropriate concentration, about 3 μl would be injected into a flask of about 270 ml. Flask 10 can be used without separate, external controlled atmosphere with a conventional atomic plasma spectroscopy system.

FIG. 2 illustrates a convenient container for storing a small amount of material during the testing procedure. Container 20 is provided with septum 22 for removal of samples by syringe for subsequent injection into flask 10 through septum 14. To provide a convenient reservoir for the needle of the syringe, the bottom portion 24 of container 20 is tapered and extended. Container 20 also is provided with ground glass opening 26 to allow container 20 to be readily filled from a storage cylinder (not shown).

FIG. 3 illustrates an adapter to facilitate transfer of material from a storage cylinder (not shown) to container 20. Adaptor 30 is provided with a fitting 32 for attachment to a storage cylinder, and ground glass fitting 34 for insertion into ground glass fitting 26 in container 20. Adaptor 30 is also fitted with tubes 36 and 38 to provide an inert atmosphere during transfer of material from the storage cylinder to container 20. A metalto-glass seal 39 connects fitting 32 to the remainder of adaptor 30.

Another embodiment of the method of analysis of the present invention is indirect analysis by decomposition of the sample. This embodiment would be more commonly used when an indication is needed of the level of impurities which are non-volatile. However, in contrast to the prior art, the indirect analysis of the present invention more closely determines the true level of impurities.

Sample preparation for indirect analysis is more readily described by reference to FIG. 4. To reaction flask 40 is added a solution of acid. The choice of acid is not critical, preferred acids being hydrochloric acid and nitric acid. The acid solution is maintained in the frozen state by beaker 41 which contains liquid nitrogen or other suitable refrigerant such as dry ice/acetone. Reaction flask 40 is provided with two ground glass openings 42 and 44. Opening 42 is fitted with a stopper which can be removed to vent gases formed during the decomposition procedure. Reaction and venting are performed in a dry argon or nitrogen purged chamber. Opening 44 is fitted with addition funnel 46. Stopper 48 having a small gap to the controlled, inert gas atmosphere is removably attached to funnel 46. Adapter 30 can be used to transfer a sample from a storage cylinder (not shown) to funnel 46 by inserting adapter 30 in place of stopper 48. The entire assembly is flushed with an inert gas and then an appropriate amount of material is transferred from the storage container to funnel 46 with stopcock 50 being in a closed position. After addition to funnel 46, adapter 30 is removed and replaced by stopper 48. Stopper 52 is placed in flask 40 after the acid solution is frozen.

The material in funnel 46 is then added dropwise with stopper 52 being removed during addition. After the addition of each drop, the reaction is allowed to subside before another drop is added. When all the material in funnel 46 has been added, the solution is allowed to melt, and then transferred to a beaker for aqueous dilution and analysis by conventional nebulization techniques.

Although the amount of material originally added to funnel 46 is not known, it is readily determined by comparison to a known standard gallium solution, which information can then be used in determining the level of impurities.

Direct analysis using an exponential dilution flask differs from indirect analysis after decomposition, and from direct analsis using an organic solvent such as xylene or hexane to dissolve the organometallic compound. Finding standards for comparison is simple where decomposition has taken place, but only impurities which completely and reliably decompose can be accurately measured. For example, tetramethylsilane (a likely contaminant of TMG) is extremely difficult to decompose, even in strong acid. Dissolution in a solvent is sufficient provided the impurities are well identified so that appropriate standards can be prepared. It is only the use of an exponential dilution flask which allows determination of impurities without knowing what form they are in, e.g., organometallic or inorganic. This is a definite advantage.

Although the above description has referred to inductively coupled plasma (ICP), the method of the present invention should also be useful with systems utilizing DC plasma or microwave plasma. Similarly, while atomic emission spectroscopy (AES) has been referred to above, the method of the present invention should also be useful with atomic absorption spectroscopy, atomic fluorescence spectroscopy, and mass spectroscopy.

To obtain a more complete understanding of the present invention, the following examples are set forth. However, it should be understood that the invention is not limited to the specific details set forth in the following examples.

EXAMPLE 1

This example illustrates direct analysis of impurities by using an exponential dilution flask (EDF) such as that illustrated in FIG 1. By syringe, 3 $\mu$l of trimethylgallium (TMC) are transferred from a container such as that in FIG. 2, to the EDF of about 270 ml which has been previously purged with argon gas. The EDF contains a magnetic stirring bar and is heated to about 40°–50° C.

After allowing the sample to vaporize, argon gas which has been flowing through a bypass is directed to flow through the exponential dilution flask at a carrier gas velocity of about 0.6 l/min and thereby feed the sample to an ICP-AES unit. The silicon concentration is determined by comparison of the silicon line which appears at 251.6 nm of the atomic emission spectra.

The exponential dilution flask results in a continually more dilute vapor being provided for analysis from which the concentration of the sample can be determined by comparison with samples of known dilution. The curve generated by an exponential dilution flask and how it is interpreted is discussed in Inman et al, referred to above. It is found that 30 seconds is the optimum time of decay to allow appropriate mathematical fitting to the dilutron cuve to provide an indication of the amount of silicon present in the sample being analyzed. The exponential relationship to concentration as a calibration technique is described by Ritter et al, above.

EXAMPLE 2

This example illustrates indirect analysis in aqueous medium. In the maner described above, about 1–1.5 ml of TMG is decomposed by dropwise addition to 30 ml of 0.5 N HCl. The HCl solution is then allowed to melt, and the acidity of the final solution adjusted to about 0.6–0.7 N. After complete dissolution of the galium comounds, the solution is transferred to a 100 ml flask diluted with distilled water. Since the exact TMG quantity transferred into aqueous phase is not known, it is determined by the TCP-AES technique using conventional aqueous standard gallium solution.

To make sure that the TMG decomposition is complete after its reaction with water, the following experiment is conducted. A known volume of aqueous solution containing decomposed TMG as described above is evaporated to dryness and treated with a few drops of concentrated $HNO_3$ and several aliquots of 30% $H_2O_2$ until the precipitate becomes white. The precipitate is then dissolved with 1% $HNO_3$ and diluted to the same volume as before. High concentrations of acid in the solution are known to depress the signal and decrease the sensitivity. Accordingly, high concentrations of acid should be avoided, solutions of 1N or less being preferred. The gallium and carbon concentrations of the solutions before and after the treatment are compared. The results are tabulated below:

| SOLUTION | GALLIUM CONCENTRATION | CARBON SIGNAL |
| --- | --- | --- |
| distilled water | <40 ng/ml | 3.4 nA |
| TMG before treatment | 14.0 mg/ml | 124 nA |
| TMG after treatment | 14.2 mg/ml | 7.3 nA |

Since the gallium concentration of the solution before and after the treament is essentially the same, and the carbon signal and thus content of the solution approaches that of the distilled water blank, this means that the organic gallium has been completely deomposed by reaction with water, and no volatile TMG remains in the aqueous phase.

From an ICP-AES analytical point of view, the solution sample is considered non-volatile since the signal of the element determined before nebulization and after nebulization (that is, the sample recovered from the drain) gives the same value each time within acceptable error.

The aqueous TMG solution is checked before and after nebulization for the following analytes: aluminum, magnesium, calcium, copper, iron. The net signals are the same indicating that no volatilization phenomenon takes place. The silicon, the most important contamination of TMG according to the direct vapor analysis of TMG, is known to be in volatile form and thus no attempt is made to determine it.

The following list sets forth the detection limits of these elements from trimethylgallium based upon three times the detection limit of single-element aqueous solution and a 2% TMG solution. The detection limit is calculated from the standard deviation of the background signal, a factor of 0.03, and the net signal and sensitivity of a silicon standard solution.

| ELEMENT | DETECTION LIMIT IN TMG |
| --- | --- |
| Aluminum | 5 µg/g |
| Iron | 2 µg/g |
| Magnesium | 0.2 µg/g |
| Copper | 2 µg/g |
| Calcium | 0.1 µg/g |

EXAMPLE 3

This example provides a comparison of direct versus indirect analysis for three TMG samples from different sources. The three samples are analyzed indirectly for all the listed impurities using the technique of Example 2, and directly for silicon using the technique of Example 1. The results are summarized as follows:

| Sample | Indirect Method Element Concentration (µg/g) | | | | | Direct Method** |
| --- | --- | --- | --- | --- | --- | --- |
|  | Al | Fe | Cu | Mg | Si | Si |
| 31 | 4.8* | 2 | 5 | 2 | 8 | 9 |
| 32 | 24 | 2 | 2 | 2 | 7 | 6 |
| 33 | 5 | 11 | 2 | 1 | 27 | 43 |

*The aluminum concentration for Sample 31 is by percent rather than µg/g.
**Measurements of silicon by the direct method are in µg/ml which is converted to µg/g by dividing by the density of TMG (1.1 g/ml).

While the invention has been described in terms of various preferred embodiments, one skilled in the art will appreciate that various modifications, substitutions, omissions, and changes may be made without departing from the spirit thereof. Accordingly, it is intended that the scope of the present in invention be limited solely by the scope of the following claims.

What is claimed is:

1. A method of analyzing a volatile, air or moisture sensitive, or pyrophoric, liquid organometallic sample for an impurity, comprising the steps of:
    A. providing (a) an exponential dilution flask comprising liquid sample receiving means, (b) a source of carrier gas selectively communicating with or isolated from said exponential dilution flask, and (c) plasma spectroscopy analysis apparatus selectively communicating with or isolated from said exponential dilution flask;
    B. isolating said exponential dilution flask from said source of carrier gas, said spectroscopy apparatus and the environment external to the exponential dilution flask;
    C. while said exponential dilution flask is isolated, introducing a volatile, air or moisture sensitive, or pyrophoric, liquid, organometallic sample into said exponential dilution flask through said liquid sample receiving means;
    D. while said flask is isolated, evaporating substantially all the liquid sample within said exponential dilution flask, thereby forming a gaseous sample contained entirely within said exponential dilution flask;
    E. establishing communication between said source of carrier gas and said exponential dilution flask, and between said exponential dilution flask and said plasma spectroscopy analysis apparatus; and
    F. introducing a flow of carrier gas into said flask from said source of carrier gas, thereby sweeping the gaseous sample from said exponential dilution flask into said spectroscopy apparatus.

2. The method of claim 1 wherein the impurity is a volatile silicon compound.

3. The method of claim 1 wherein the liquid organometallic sample is trimethylgallium.

4. The method of claim 1 wherein said plasma spectroscopy apparatus comprises an atomic emission spectroscopy apparatus.

5. The method of claim 1, wherein said liquid sample receiving means comprises a septum.

6. The method of claim 1, wherein said carrier gas is argon.

7. The method of claim 1, wherein an outlet valve is provided for selectively isolating said exponential dilution flask from said spectroscopy apparatus or establishing communication between said exponential dilution flask and said spectroscopy apparatus.

8. The method of claim 7, wherein an inlet valve is provided for selectively isolating said exponential dilution flask from said source of carrier gas or establishing communication between said exponential dilution flask and said source of carrier gas.

9. The method of claim 8, wherein said isolating step is executed by closing said inlet and outlet valves and wherein said step of establishing communication between said source of carrier gas and said exponential flask is executed by opening said inlet and outlet valves.

* * * * *

UNITED STATES PATENT AND TRADEMARK OFFICE
CERTIFICATE OF CORRECTION

PATENT NO.   : 4,688,935
DATED        : August 25, 1987
INVENTOR(S)  : Barnes et al.

It is certified that error appears in the above-identified patent and that said Letters Patent is hereby corrected as shown below:

Column 6, line 35, "dilutron cuve" should be --dilution curve--.

Column 6, line 48, "galium" should be --gallium--.

Column 6, line 50, insert --and-- before "diluted".

Column 6, line 52, "TCP-AES" should be --ICP-AES--.

Column 8, line 25, after "said" insert --exponential dilution--.

Column 8, line 35, after "said and before "flask" insert --exponential dilution--.

Column 8, line 62, "valves" should be --valves,--.

Signed and Sealed this
Twenty-third Day of January, 1990

Attest:

JEFFREY M. SAMUELS

*Attesting Officer*   *Acting Commissioner of Patents and Trademarks*